United States Patent [19]
Sturman et al.

[11] Patent Number: 5,246,427
[45] Date of Patent: Sep. 21, 1993

[54] SAFETY HYPODERMIC NEEDLE AND SHIELDING CAP ASSEMBLY

[76] Inventors: Martin F. Sturman, 7315 Granite Rd., Melrose Park, Pa. 19126; Maurice S. Kanbar, 4 E. 77th St., New York, N.Y. 10021; Robert J. Cohn, 61 Sterling Ave., Dallas, Pa. 18612; Albert Kolvites, R.R. 3 Box 117A Yeager Rd., Mountaintop, Pa. 18707

[21] Appl. No.: 981,401

[22] Filed: Nov. 25, 1992

[51] Int. Cl.⁵ .............................................. A61M 5/32
[52] U.S. Cl. .................................... 604/192; 604/198
[58] Field of Search ............... 604/192, 198, 110, 187, 604/263

[56] References Cited

U.S. PATENT DOCUMENTS 5,013,305 5/1991 Opie et al. .
5,092,851 3/1992 Ragner .......................... 604/192

*Primary Examiner*—John D. Yasko
*Attorney, Agent, or Firm*—Michael Ebert

[57] ABSTRACT

A safety hypodermic needle and shielding cap assembly for a standard syringe whose fluid chamber is provided at its front end with a projecting nozzle coaxial with a coupling socket. The assembly includes a needle-supporting hub whose hollow base is coupled to the socket of the syringe, the nozzle then communicating with the needle. Encircling the hub and attached thereto is a resilient actuator collar defining an annular space within which is received the lower end of a helical spring surrounding the needle extending from the hub. The upper end of the spring is received in the cavity of a shielding cap having a center bore therein through which the needle is passable. The cap is tethered by opposing lines of unequal length to the collar. In the retracted mode of the assembly, the spring is compressed by the cap, which is provided with a pair of opposed lugs that are inserted in corresponding slots in the long sides of the collar, thereby latching the cap and exposing the needle, so that it can be injected into a patient. After the needle is withdrawn, the assembly is put in its operative mode by squeezing the collar at its short sides to disengage the lugs and release the cap which is carried by the expanding spring to a position covering the needle point, the tether lines of unequal length acting to cant the cap to offset its bore with respect to the needle point.

7 Claims, 4 Drawing Sheets

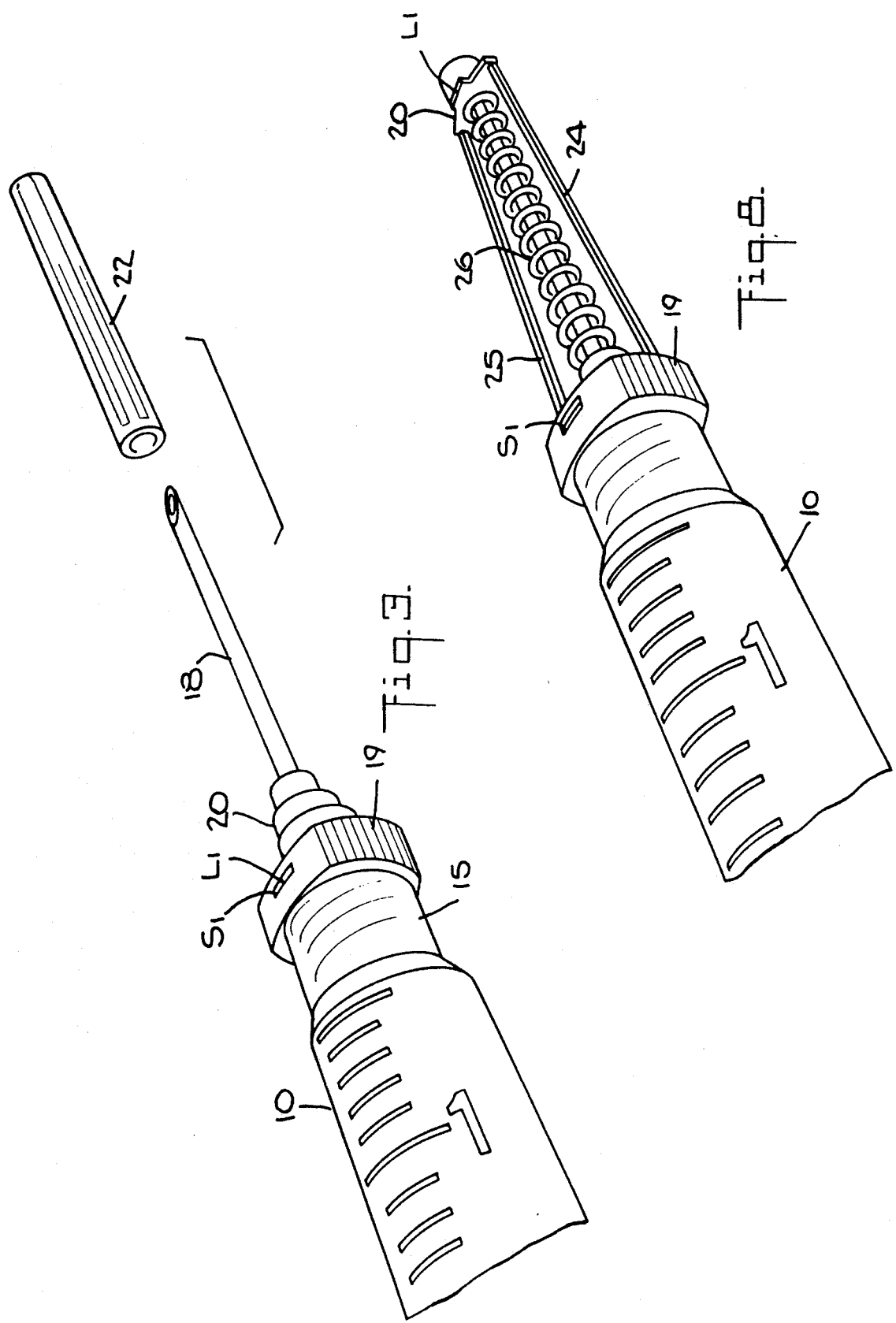

SAFETY HYPODERMIC NEEDLE AND SHIELDING CAP ASSEMBLY

BACKGROUND OF INVENTION

1. Field of Invention

This invention relates generally to hypodermic syringes, and in particular to a safety hypodermic needle and shielding cap assembly, which in its retracted mode permits the user to inject the needle into a patient, and which after the needle is withdrawn from the patient, in its operative mode then shields the point of the needle to prevent accidental sticks thereby.

2. Status of Prior Art

A hypodermic needle is usable for intravenous, subcutaneous and intramuscular injection of fluids, or the removal of blood (venipuncture), body fluids or abnormal collections thereof, the needle being of hollow construction and having a slanted open point. When the needle is mounted on a syringe, it is adapted to aspirate or inject fluids for diagnostic or therapeutic purposes.

Disposable hypodermic needles are now mass produced at low cost, many billions of such syringes being used every year in the health care field. While the modern hypodermic syringe now includes a fluid chamber molded of synthetic plastic material rather than glass, its basic design remains much as it was in 1853 when invented by Charles Pravaz, a French physician.

In a hypodermic syringe of standard design, a piston is slidable within a cylindrical fluid chamber, the shank of the piston extending beyond the rear end of the chamber and terminating in a handle. The front end of the chamber is provided with a projecting nozzle that is coaxial with an internally-threaded socket adapted to receive a needle-supporting hub. When the hub is screwed into the socket, the nozzle is then projected therein to communicate with the needle.

A hypodermic needle and a syringe attached thereto are distributed in sterile condition within a plastic bubble package to protect them against contamination in storage and shipment. In addition, the needle is enclosed in a removable overcap whose inlet end snaps onto the needle hub. Thus, after the hypodermic needle and syringe are removed from its package, in order to put it to use one must first remove the overcap to expose the needle. After the hypodermic syringe has been injected into a patient and then withdrawn, it is the usual practice before discarding the syringe to place the overcap back on the needle hub so that those thereafter handling discarded syringes for purposes of disposal will not be pricked thereby.

When a sterile hypodermic needle is injected into a patient suffering from hepatitis or other infectious diseases and the needle is then withdrawn from the patient, it may be contaminated with infectious agents. Hence, should the handler inadvertently prick himself with this contaminated needle, the consequences may be serious.

The possibility of accidental contamination by needle puncture of the skin of those individuals in the health care field who employ hypodermic syringes for venipuncture, the withdrawal of body fluids or for any other medical purpose is fairly high and represents a significant risk. Thus, physicians, nurses, laboratory personnel, paramedics and others involved in the care and treatment of patients are in danger of being accidentally inoculated with infectious microorganisms by contaminated needles.

Most accidental needle sticks occur when the needles are being recapped; for to do so properly, one must first align the needle with the relatively small diameter inlet of the overcap. Should the needle be misaligned, as may well happen should the handler be careless, distracted or fatigued, the point of the needle will not enter the overcap but may instead puncture the finger of the handler.

It is well established that in the last 25 year the risks involved in handling hypodermic syringes has markedly increased. Statistics indicate very high rates of hepatitis B infection among medical and laboratory personnel by reason of this accidental mode of disease transmission. Medical personnel who care for patients suffering from AIDS run a still higher risk; for a needle contaminated with HIV (Human immunodeficiency virus) is a source of great danger. Should the handler of this needle be accidentally punctured, he faces the prospect of contracting a disease currently having a 100% mortality rate as compared, say, to the 5 to 10% mortality rate of hepatitis B.

The 1988 patent to Wanderer et al., U.S. Pat. No. 4,731,059, is concerned with preventing needle sticks, and for this purpose provides a shield which is slidable from a position covering the needle to a position overlying the fluid chamber so that the needle can be exposed when put to use and thereafter shielded. A somewhat similar arrangement is disclosed in the 1987 patent to Fox, U.S. Pat. No. 4,695,274, which shows a retractable safety jacket for a hypodermic needle.

One practical problem with the safety shields or needle guards of the type disclosed in the Wanderer et al. and Fox patents is that when the needle is exposed so that the syringe can be put to use, the retracted guard then covers and obscures the transparent chamber which is graduated so that one can determine the amount of fluid that is contained therein. Hence this guard interferes with the proper operation of the hypodermic syringe.

But the more serious drawbacks of these prior art needle guard arrangements is that in order to accommodate the guard, they require a modification of the basic configuration of the standard hypodermic syringe. Thus in one commercially available form of safety hypodermic syringe having a needle guard, the needle is mounted on an elongated extension tube projecting from the fluid chamber, so that when the guard is retracted, it overlies the extension tube, not the fluid chamber. Hence, fluid from the chamber must be conducted through the extension tube which, by its very nature, elongates the hypodermic syringe, making it more difficult to handle.

To provide a safety hypodermic needle and shield assembly that is compatible with a standard syringe, the patent to Spier et al., U.S. Pat. No. 4,921,490, and the patent to Sturman et al., U.S. Pat. No. 4,863,435, disclose an assembly having a needle-supporting hub whose hollow base is coupled to the socket of the syringe so that the projecting nozzle then communicates with the needle.

Anchored on this hub and surrounding the needle extending therefrom is a helical spring at whose upper end is a shield, the length of the spring being such as to place the shield in front of the needle point. In the retracted mode of the assembly, the spring is compressed and latched to expose the needle so that it can be injected into a patient. In the operative mode of the assembly, which takes effect after the needle is withdrawn from the patient and the spring is released, the shield then is placed in front of the needle point to prevent accidental sticks.

The safety needle and shield assemblies disclosed in the Spier et al. and Sturman et al. patents have distinct advantages, for they require no modification of the standard syringe. But they have practical drawbacks. One such drawback is that the latching mechanism which releases the spring is so bulky that it prevents injection of the hypodermic needle into a patient at a low angle, as is sometimes necessary. Another drawback is that when the assembly is in its operative position, it may still be possible to elongate the spring and cause the needle to pass through the protective shield and prick the handler.

SUMMARY OF INVENTION

In view of the foregoing, the main object of this invention is to provide a safety hypodermic needle and shielding cap assembly for a syringe which obviates the danger of a handler thereof being accidentally pricked by the point of the needle after it has been injected in a patient and then withdrawn.

More particularly, an object of this invention is to provide a safety hypodermic needle and shielding cap assembly of the above type which requires no basic modification of the design of a standard syringe and which can be manufactured inexpensively on a mass production basis.

Also an object of the invention is to provide an assembly of the above type which can readily be coupled to the fluid chamber of a standard hypodermic syringe.

A significant feature of the invention is that the shielding cap is so tethered that in the operative mode of the assembly when the cap covers the point of the needle, the cap is then canted so that the bore therein through which the needle is passable is then offset with respect to the needle point and the point cannot go through the bore.

Briefly stated, these objects are attained in a safety hypodermic needle and shielding cap assembly for a standard syringe whose fluid chamber is provided at its front end with a projecting nozzle coaxial with a coupling socket. The assembly includes a needle-supporting hub whose hollow base is coupled to the socket of the syringe, the nozzle then communicating with the needle. Encircling the hub and attached thereto is a resilient actuator collar defining an annular space within which is received the lower end of a helical spring surrounding the needle extending from the hub. The upper end of the spring is received in the cavity of a shielding cap having a center bore therein through which the needle is passable.

The cap is tethered by opposing lines of unequal length to the collar. In the retracted mode of the assembly, the spring is compressed by the cap, which is provided with a pair of opposed lugs that are inserted in corresponding slots in the long sides of the collar, thereby latching the cap and exposing the needle, so that it can be injected into a patient. After the needle is withdrawn, the assembly is put in its operative mode by squeezing the collar at its short sides to disengage the lugs and release the cap which is carried by the expanding spring to a position covering the needle point, the tether lines of unequal length acting to cant the cap to offset its bore with respect to the needle point.

BRIEF DESCRIPTION OF DRAWINGS

For a better understanding of the invention as well as other objects and further features thereof, reference is made to the following detailed description to be read in conjunction with the accompanying drawing, wherein:

FIG. 3 shows the assembly mounted on the syringe with the needle cover removed so that now the assembly is in its retracted mode in condition for needle injection;

FIG. 8 shows the assembly in its operative mode mounted on the syringe; and

DESCRIPTION OF INVENTION

Figure 1:
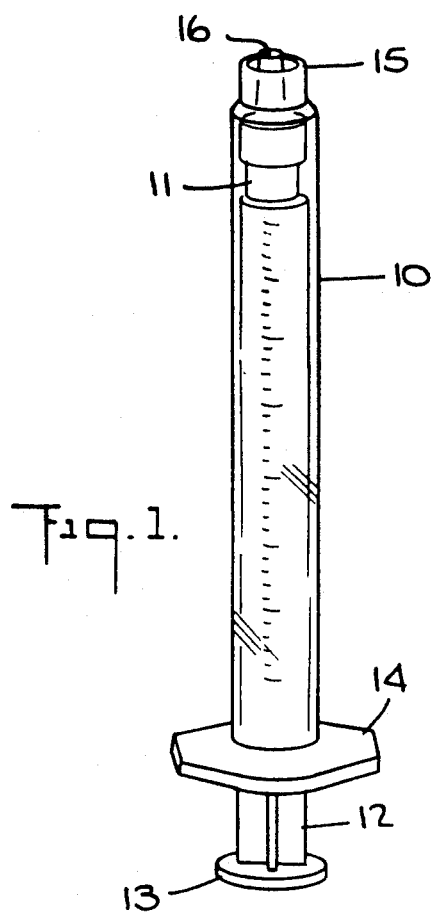
FIG. 1 illustrates a standard hypodermic syringe.

Referring now to FIG. 1, there is shown a standard hypodermic syringe usable with a safety hypodermic needle and shielding cap assembly in accordance with the invention.

Included in the syringe is a cylindrical fluid chamber 10 formed of transparent, synthetic plastic material such as polyethylene, polypropylene, polystyrene or PVC having indicia thereon to indicate the level of fluid in the chamber. Slidable within the chamber is a piston 11 for ejecting fluid from the chamber or drawing fluid therein, the piston having a shank 12 which extends beyond the open end of the chamber and terminates in a handle 13.

As is conventional, the rear end of chamber 10 is provided with a flange 14 so that to manipulate the piston to draw fluid from a patient or to inject fluid into the patient, the user holds the flange with the fingers of one hand while grasping handle 13 with the fingers of the other hand. At the front end of chamber 10 is an internally-threaded cylindrical socket 15, and coaxially disposed therein is a nozzle 16 whose inlet communicates with the interior of the chamber.

Figure 4:
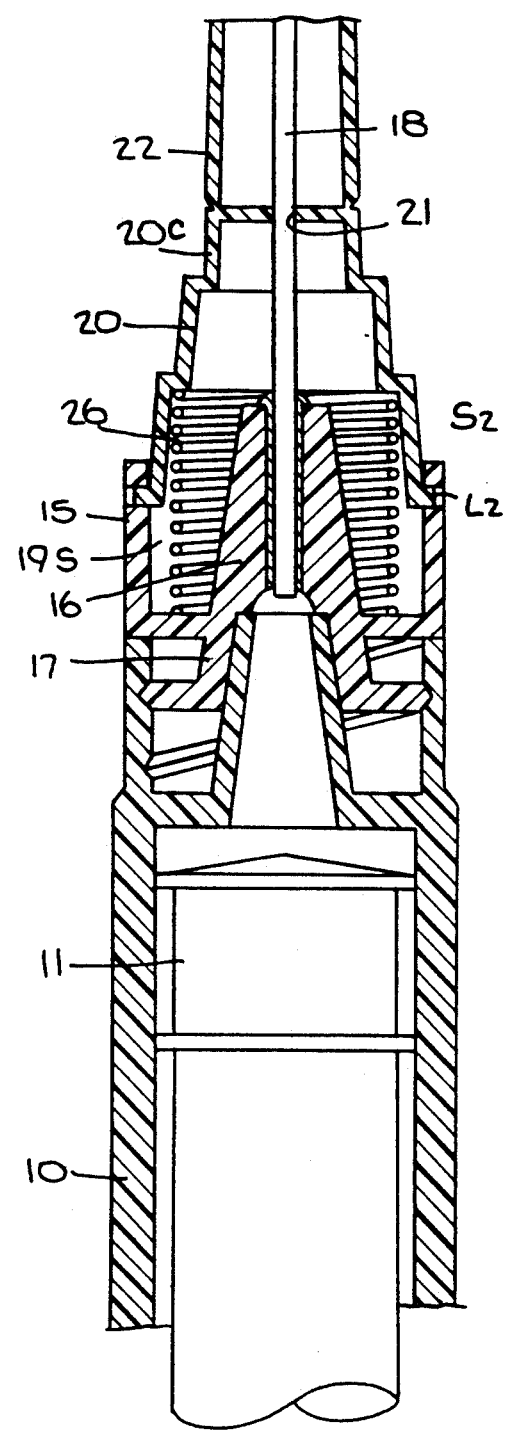
FIG. 4 is a sectional view of the assembly in its retracted mode, mounted on the syringe.
Figure 2:
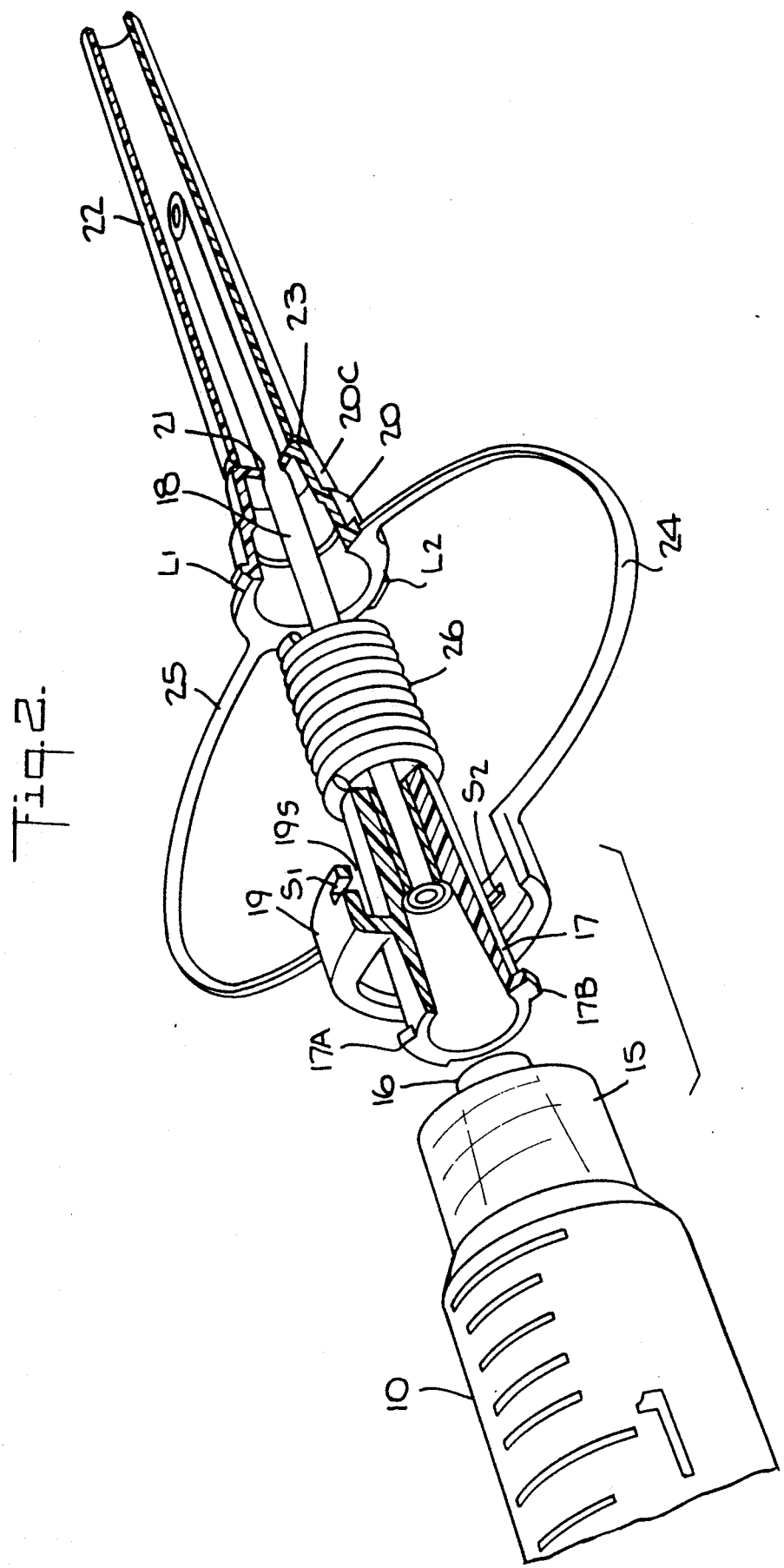
FIG. 2 is a perspective view, partly cut away, of a hypodermic needle syringe and cap assembly in accordance with the invention.

As shown in FIGS. 2 and 4, a safety hypodermic needle and shielding cap assembly in accordance with the invention includes a hollow, tapered hub 17 having at its lower end a pair of teeth 17A and 17B which project from diametrically-opposed positions. These teeth act as an external thread to engage the internal threading on the coupling socket 15 of the syringe, making it possible to mount the assembly on the syringe, a shown in FIG. 3.

Supported on hub 17 and extending axially therefrom is a hypodermic needle 18 the lower end of which is disposed within the hub cavity. When, therefore, hub 17 is screwed into socket 15 of the syringe, nozzle 16, coaxially disposed within the socket, projects into the hub cavity to communicate with the needle so that fluid may be fed into the fluid chamber of the needle, or fed out of the chamber into the needle, depending on how the syringe is operated.

An actuator collar 19 of resilient material and having an elliptical shape encircles hub 17 at an intermediate position thereon. The collar is attached at its lower end to the hub to define an annular space 19S between the outer wall of the hub and the inner wall of the collar.

Above hub 17 is a shielding cap 20 having a stepped formation to define a crown 20C. Crown 20C is provided with a central bore 21 through which needle 18 is passable. Integral with crown 20C and extending therefrom is a tubular cover 22 which surrounds the needle and extends beyond its point, so that when the cover is in place, the needle is fully protected.

An annular groove 23 between cap crown 20C and cover tube 22 provides a weakening juncture, so that, as shown in FIG. 3, cover tube 22 may be readily broken off to expose needle 18 before the assembly is put to use. This detachable cover dispenses with the need for a large diameter overcap conventionally used with a standard hypodermic syringe.

Shielding cap 20 is tethered to actuating collar 19 by means of two flexible lines or filaments 24 and 25. These tether lines are of unequal length, for reasons to be later explained.

The upper extremities of lines 24 and 25 are joined at diametrically-opposed positions to the lower end of cap 20. The lower extremities of lines 24 and 25 are joined to the short sides of the elliptical collar 19 at the upper end of the collar. The lower end of cap 20 is provided with a pair of lugs $L_1$ and $L_2$ at opposed positions intermediate the points at which the upper extremities of lines 24 and 25 are joined to the cap. These lugs are insertable into corresponding positioned slots $S_1$ and $S_2$ on the long sides of the elliptically-shaped collar 19.

Surrounding needle 18 between collar 19 and cap 20 is a helical spring 26 (shown in its compressed state), the lower end of which is received in cavity 19S of the collar, the upper end being received in the lower cavity of cap 20.

Figure 5:
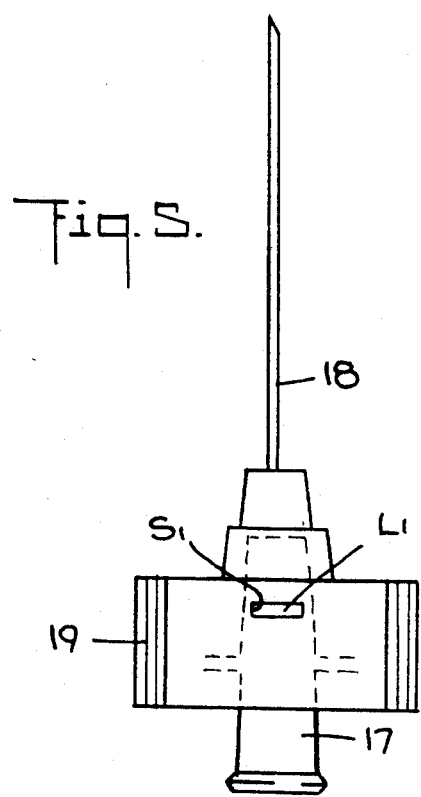
FIG. 5 shows the assembly in the retracted mode separated from the syringe.

In the retracted mode of the assembly, as shown in FIGS. 4 and 5, helical spring 26 is compressed by cap 20 which is latched to collar 19, lugs $L_1$ and $L_2$ of the cap then being received in slots $S_1$ and $S_2$ on the collar. The portion of needle 18 which extends beyond the latched shielding cap 20 is then fully exposed and can be injected into a patient. And because no part of the assembly projects laterally beyond the cylindrical wall of fluid chamber 10 of the syringe to which the assembly is coupled, it is possible to inject patients at low angles at which the fluid chamber of the syringe is close to the skin.

Figure 9:
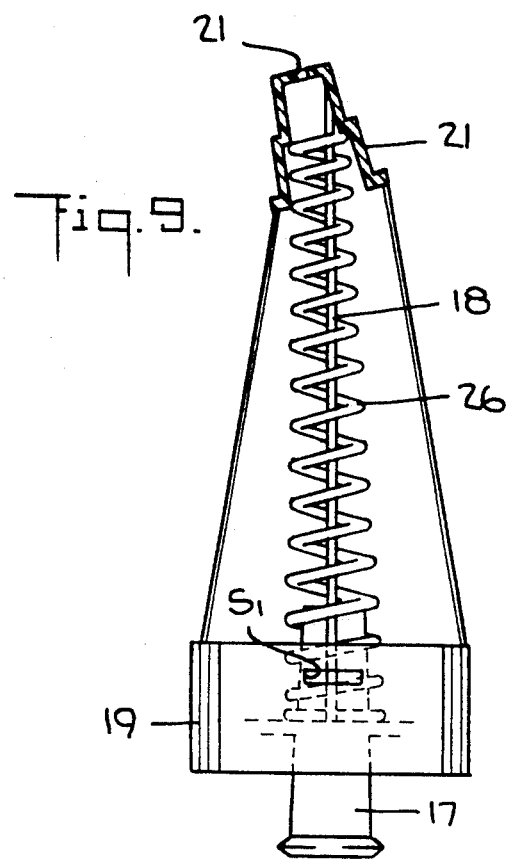
FIG. 9 shows the assembly in its operative mode separated from the syringe.

When the needle is withdrawn from the patient, it then may be contaminated, and it is now necessary to protect the handler of the hypodermic syringe from accidental pricks. To this end, the assembly is put into its operative or shielding mode in which, as shown in FIGS. 8 and 9, shielding cap 20 covers the point of the needle and is canted with respect to this point.

Hence, if pressure is applied to the cap, since the bore 21 in the crown 20C of the cap is now out of line with the point of the needle, spring 26 cannot be compressed to permit the needle point to pass out of the bore.

To switch the assembly from its retracted or needle injection mode, as shown in FIG. 3, to its operative or shielding mode, as shown in FIG. 8, collar 19 is squeezed by applying finger pressure to the short sides of the elliptical collar. In the retracted mode, lugs $L_1$ and $L_2$ on cap 20 are inserted in slots $S_1$ and $S_2$ of the collar, these slots being on the long sides of the collar, as shown in FIG. 6.

Figure 7:
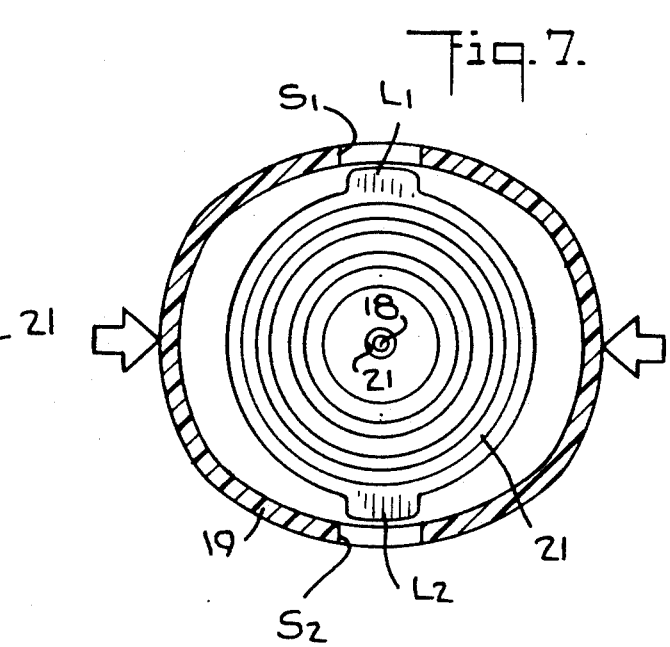
FIG. 7 shows the relationship between the actuator collar and the shielding cap after the collar has been squeezed by a user to put the assembly in its operative mode.

When, as shown in FIG. 7, finger pressure is applied to the short sides of the collar to squeeze the collar so that the long sides then bulge out, this action disengages the lugs from the slots and frees the latched cap, which is now advanced by the expanding spring 26 to its shielding position in front of the needle point. But because tether line 24 is shorter than tether line 25, this causes cap 20 tethered by these lines to tilt or cant, thereby offsetting bore 21 in the crown of the cup with respect to the needle point and ensuring a proper shielding action.

In practice, all components of the assembly may be molded of resilient, synthetic, plastic material, such as polyethylene or polyvinyl chloride, filaments 24 and 25 being of the same material and being integrated with the cap and the collar.

Figure 6:
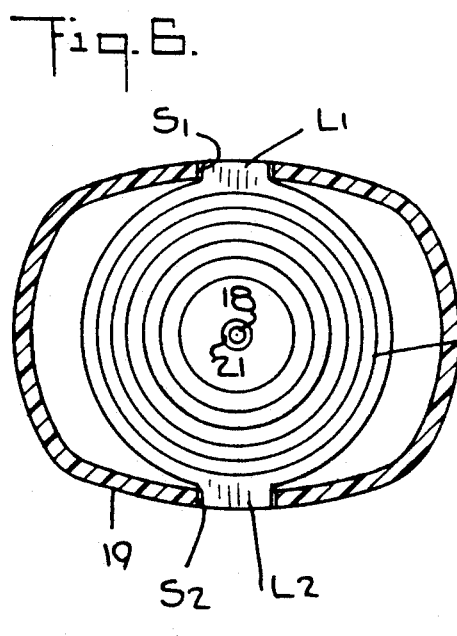
FIG. 6 is a schematic view of the actuator collar and the shielding cap of the assembly in the retracted mode.

It is to be noted that collar 19, as shown in FIGS. 5 and 6, has a thumbscrew shape. This facilitates the engagement of the needle assembly to the syringe, particularly if the fingers of the operator are wet and slippery.

While there has been shown and described a preferred embodiment of a safety hypodermic needle and shielding cap assembly in accordance with the invention, it will be appreciated that many changes and modifications may be made therein without, however, departing from the essential spirit thereof.

We claim:

1. In combination with a standard syringe whose fluid chamber has a piston slidable therein and is provided at its front end with a projecting nozzle and a cylindrical, coupling socket concentric therewith, a safety hypodermic needle and shielding cap assembly adapted to prevent accidental stick by the point of the needle after the needle has been injected into a patient and then withdrawn, said assembly comprising:

(a) a hub supporting the needle and provided with a hollow base receivable in the socket of the syringe whereby the nozzle then projects in the hollow base to communicate with the needle to conduct fluid from the chamber into the needle or to conduct fluid from the needle into the chamber;
   (b) a collar encircling the hub and attached thereto to define an annular space between the hub and the collar, said collar being provided with actuatable latching means;
   (c) a shielding cap having a bore through which the needle is passage to permit the cap to shift from a latched position at which it engages the collar, to an operative position in front of the needle;
   (d) a helical spring surrounding the needle, one end of the spring being received in the annular space, the other end being received within the cap; and
   (e) means to tether the cap to the collar, whereby when the cap is unlatched from the collar, the spring then expands to carry the tethered cap to its operative position, the tether means acting to cant the cap at its operative position to offset the bore with respect to the needle.

2. An assembly as set forth in claim 1, wherein said socket is internally threaded and the hub includes a base having a pair of opposed teeth which act as external threading to engage the internal threading of the socket.

3. An assembly as set forth in claim 1, wherein said collar is formed of resilient material and has an elliptical shape, the long sides of the collar having slots therein to receive lugs disposed at corresponding positions on said cap and thereby latch the cap, said cap being unlatched when the collar is squeezed by finger pressure applied to its short sides, causing the long sides of the collar to bulge out and thereby effect disengagement of the lugs.

4. An assembly as set forth in claim 1, wherein said tether means is constituted by two filaments of unequal length, whereby when the cap is in its operative position, the cap is canted to offset the bore in the cap with respect to the needle.

5. An assembly as set forth in claim 4, wherein said cap, said collar, said hub and said filaments are all fabricated of synthetic plastic material.

6. An assembly as set forth in claim 5, wherein said filaments are integral with said cap and collar.

7. An assembly as set forth in claim 1, in which the hub is tapered and has a stepped formation creating a crown having a center bore therein.

* * * * *